(12) United States Patent
Tamez et al.

(10) Patent No.: US 10,786,611 B2
(45) Date of Patent: Sep. 29, 2020

(54) VAD INTEGRATED FLOW SENSOR

(71) Applicant: HeartWare, Inc., Miami Lakes, FL (US)

(72) Inventors: Dan Tamez, Plantation, FL (US); Neil Voskoboynikov, Pembroke Pines, FL (US)

(73) Assignee: HeartWare, Inc., Miami Lakes, FL (US)

( * ) Notice: Subject to any disclaimer, the term of this patent is extended or adjusted under 35 U.S.C. 154(b) by 291 days.

(21) Appl. No.: 15/834,487

(22) Filed: Dec. 7, 2017

(65) Prior Publication Data

US 2018/0099077 A1    Apr. 12, 2018

Related U.S. Application Data

(63) Continuation of application No. 15/406,078, filed on Jan. 13, 2017, now Pat. No. 9,861,730, which is a
(Continued)

(51) Int. Cl.
*A61M 1/10* (2006.01)
*A61M 1/12* (2006.01)

(52) U.S. Cl.
CPC ............ *A61M 1/1086* (2013.01); *A61M 1/10* (2013.01); *A61M 1/1008* (2014.02);
(Continued)

(58) Field of Classification Search
CPC .............. A61M 1/1086; A61M 1/1008; A61M 1/1036; A61M 1/122; A61M 1/10;
(Continued)

(56) References Cited

U.S. PATENT DOCUMENTS 4,068,521 A * 1/1978 Cosentino .............. A61B 8/481
                                                          600/437
4,752,690 A * 6/1988 James ................. A61M 1/3626
                                                          250/341.5
(Continued)

FOREIGN PATENT DOCUMENTS

EP      1046403 A1    10/2000
JP      05068709       3/1993

OTHER PUBLICATIONS

International Search Report issued by the International Searching Authority (ISA/US) dated Dec. 19, 2013 in connection with International Application No. PCT/US2013/058253.
(Continued)

*Primary Examiner* — Carl H Layno
*Assistant Examiner* — Erin M Piateski
(74) *Attorney, Agent, or Firm* — Christopher & Weisberg, P.A.

(57) ABSTRACT

A blood pump with an integrated flow sensor is provided. The blood pump may include an implantable pump for pumping blood having a housing, a flow path extending within the housing and at least one movable element within the housing for impelling blood along the flow path and a sensor for measuring the flow rate of blood through the pump. According to one embodiment, the sensor may be mounted to the housing of the pump. In accordance with a further embodiment, the housing may have an exterior surface defining a cavity, and the sensor may be located within the cavity.

17 Claims, 7 Drawing Sheets

Related U.S. Application Data continuation of application No. 14/019,219, filed on Sep. 5, 2013, now Pat. No. 9,579,432.

(60) Provisional application No. 61/697,087, filed on Sep. 5, 2012.

(52) U.S. Cl.
CPC .......... *A61M 1/1036* (2014.02); *A61M 1/122* (2014.02); *A61M 1/101* (2013.01); *A61M 1/1031* (2014.02); *A61M 2205/0211* (2013.01); *A61M 2205/3334* (2013.01); *A61M 2205/3375* (2013.01)

(58) Field of Classification Search
CPC ................ A61M 1/1031; A61M 1/101; A61M 2205/0211; A61M 2205/3334; A61M 2205/3375
USPC .......................................................... 600/16
See application file for complete search history.

(56) References Cited

U.S. PATENT DOCUMENTS

| | | | |
|---|---|---|---|
| 5,078,148 A | 1/1992 | Nassi et al. | |
| 6,190,319 B1 | 2/2001 | Goldowsky | |
| 7,575,423 B2 | 8/2009 | Wampler | |
| 7,976,271 B2 | 7/2011 | LaRose et al. | |
| 8,007,254 B2 | 8/2011 | LaRose et al. | |
| 8,419,609 B2 | 4/2013 | Shambaugh, Jr. et al. | |
| 8,449,444 B2 | 5/2013 | Poirier | |
| 2005/0107658 A1* | 5/2005 | Brockway | A61M 1/1086 600/16 |
| 2008/0021325 A1* | 1/2008 | Drost | A61B 5/021 600/454 |
| 2008/0133006 A1* | 6/2008 | Crosby | A61M 1/101 623/3.13 |
| 2010/0222634 A1 | 9/2010 | Poirier | |
| 2010/0240944 A1 | 9/2010 | Maschke | |
| 2011/0178361 A1 | 7/2011 | Yomtov | |
| 2011/0257579 A1 | 10/2011 | Rossi et al. | |

OTHER PUBLICATIONS

Written Opinion of the International Searching Authority issued by the International Searching Authority (ISA/US) dated Dec. 19, 2013 in connection with International Application No. PCT/US2013/058253.

Chinese Office Action and Search Report for Application No. 201380057534.1 dated Mar. 3, 2016.

Extended European Search Report for Application No. 13835446.9 dated May 4, 2016.

Japan Office Action dated Jun. 27, 2017, corresponding Patent Application No. 2015-531182.

* cited by examiner

VAD INTEGRATED FLOW SENSOR

CROSS-REFERENCE TO RELATED APPLICATIONS

This application is a continuation of U.S. patent application Ser. No. 15/406,078 filed Jan. 13, 2017, now U.S. Pat. Ser. No. 9,861,730, issued Jan. 9, 2018, which application is a continuation of U.S. patent application Ser. No. 14/019219, filed Sep. 5, 2013, now U.S. Pat. No. 9,579,432 issued Feb. 28, 2017, which application is related to and claims priority from Provisional Patent Application Ser. No. 61/697087, filed Sep. 5, 2012, the entirety of all of which are incorporated herein by reference.

BACKGROUND OF THE INVENTION

The present invention relates to blood pumps usable as implantable ventricular assist devices, and more particularly to an improved blood pump device with an integrated ultrasonic flow sensor.

In certain disease states, the heart lacks sufficient pumping capacity to maintain adequate blood flow to the body's organs and tissues. For example, conditions such as ischaemic heart disease and hypertension may leave the heart unable to fill and pump efficiently. This condition, also called congestive heart failure, may lead to serious health complications, including respiratory distress, cardiac asthma, and even death. In fact, congestive heart failure is one of the major causes of death in the Western world.

This inadequacy of the heart can be alleviated by providing a mechanical pump also referred to as a ventricular assist device ("VAD") to supplement the pumping action of the heart. VADs may be used to assist the right ventricle, the left ventricle, or both. For example, a VAD may assist the left ventricle by mechanically pumping oxygenated blood from the left ventricle into the aorta. In this case, the pump is implanted within the body of the patient, an inflow conduit is attached to the left ventricle, and an outflow conduit is attached to the aorta. For example, where the pump is implanted below the heart or at the bottom of the heart, the outflow conduit may be a flexible conduit extending generally upwardly, from the outlet of the pump to the aorta. The pump receives blood from the left ventricle and then pushes it into the aorta for distribution throughout the body. This reduces the strain on the heart by reducing the volume of blood that the heart is responsible for moving.

U.S. Pat. Nos. 7,575,423, 7,976,271, 8,007,254, and 8,419,609, the disclosures of which are hereby incorporated by reference, disclose certain rotary blood pumps which can be used as ventricular assist devices. These pumps are electrically powered. Typically, these and other electrically powered implantable pumps are connected through a cable, commonly referred to as a "driveline", to a control device which supplies electric power to the pump and controls its operation. The control device may be external to the patient's body, in which case the driveline extends through the skin. It has also been proposed to use implanted control devices which receive power from an external source by means of an implanted induction coil.

It is desirable to monitor certain parameters of the pump, including for instance the rate of blood flow through the VAD. Flow information can be used to detect abnormal operating conditions, such as blockage of the outflow conduit or a "suction" condition, where the left ventricle is not refilled fast enough to keep the pump supplied with blood, and also can be used to provide feedback control of the pump. However, blood flow through a VAD is difficult to monitor because it often cannot be measured directly. It would not be desirable to install a bulky sensor in the path of the flowing blood, as the sensor could obstruct the blood flow and reduce the effectiveness of the pump.

One solution that has been proposed is to measure blood flow indirectly. This can be achieved by measuring blood pressure at both the inflow and outflow sections of the pump, and then mathematically computing blood flow. Pressure sensors have been incorporated into VADs for the purpose of monitoring blood flow through the VAD. Blood flow also can be determined indirectly from operational parameters of the pump as, for example, the speed of the pump and the power used by the pump.

Other solutions have been proposed that involve measuring blood flow through the pump directly. This can be achieved, for instance, through the use of an ultrasonic flow probe. For example, it has been proposed to provide an ultrasonic flow probe around mounted on the outflow cannula. Similarly, European Patent EP1046403 discloses a blood circulation device with ultrasonic flow sensors attached to the inflow cannula or "blood feeding pipe." In these proposed solutions, blood flow can be monitored directly for enhanced control over the therapeutic qualities of the pump. However, these solutions require an additional structure to hold the ultrasonic flow probe. Moreover, as further discussed below, certain types of ultrasonic flow measurement can be used only in a rigid conduit. Where the flow is measured along a flexible conduit, the additional structure typically must have appreciable bulk to hold a portion of the flexible conduit in a fixed configuration. Also, these arrangements require an additional cable extending to the additional structure housing the flow probe. These factors make it more difficult to implant the system in the body.

Thus, despite very considerable effort devoted in the art to development of ventricular assist devices, further improvement would be desirable. Particularly, there is a need for a VAD which can provide the benefits of direct flow measurement without substantially increasing the difficulty of implanting the device.

SUMMARY OF THE INVENTION

One aspect of the present invention provides a blood pump with an integrated flow sensor. The blood pump according to this aspect of the invention desirably includes an implantable pump for pumping blood having a rigid housing, a flow path extending within the housing and at least one movable element within the housing for impelling blood along the flow path, and a sensor for measuring the flow rate of blood through the pump. In this aspect of the invention, the sensor may be mounted to the housing of the pump.

A further aspect of the invention provides a blood pump including a first housing element having an interior surface at least partially defining the flow path and having an exterior surface defining a cavity. In this aspect, the sensor may be located within the cavity. The sensor may also include, for example, one, two or more ultrasonic transducers.

Yet another aspect of the invention includes a blood pump having a first and second platform. According to this aspect, the flow path may extend along a flow path axis extending in upstream and downstream directions. The first housing element may define a first platform facing downstream at an oblique angle to the flow path axis and a second platform surface upstream at an oblique angle to the flow path axis.

Further, the ultrasonic transducers may include a first transducer mounted to the first platform and a second transducer mounted to the second platform. The platforms may, for example, have a slope of substantially 45 degrees to the flow path axis. The ultrasonic transducers may also be mounted to the platforms with an adhesive.

A further aspect of the invention also provides a second housing element. In this aspect, the first and second housing elements may cooperatively define at least a portion of the flow path. Further, the transducers may be arranged such that the ultrasound emitted from one of the transducers passes through the flow path to the second housing element and reflects from the second housing element and passes to the other one of the transducers. The housing may further include a cover overlying the cavity in the first housing element. Optionally, an electronic circuit may be disposed within the cavity and may also be connected to the sensor.

A still further aspect of the invention includes a blood pump having an inflow end and an outflow end. The sensor may be mounted adjacent the outflow end of the flow path. The sensor may also be mounted adjacent to the inflow end of the flow path. In some aspects of the invention, the pump may be a rotary pump.

A further aspect of the invention may provide a blood pump having one or more electrical elements for moving the movable element. In this aspect, the device may also include an external control unit that powers the electrical elements. Further, the device may also include a driveline for connecting the pump and the one or more ultrasonic transducers to the external control unit. The sensor may be connected to the control unit through the driveline. The driveline may also be the only connection between the pump and the control unit.

These and other aspects of the invention will be more readily understood with reference to the detailed description taken below.

DETAILED DESCRIPTION

Figure 1:
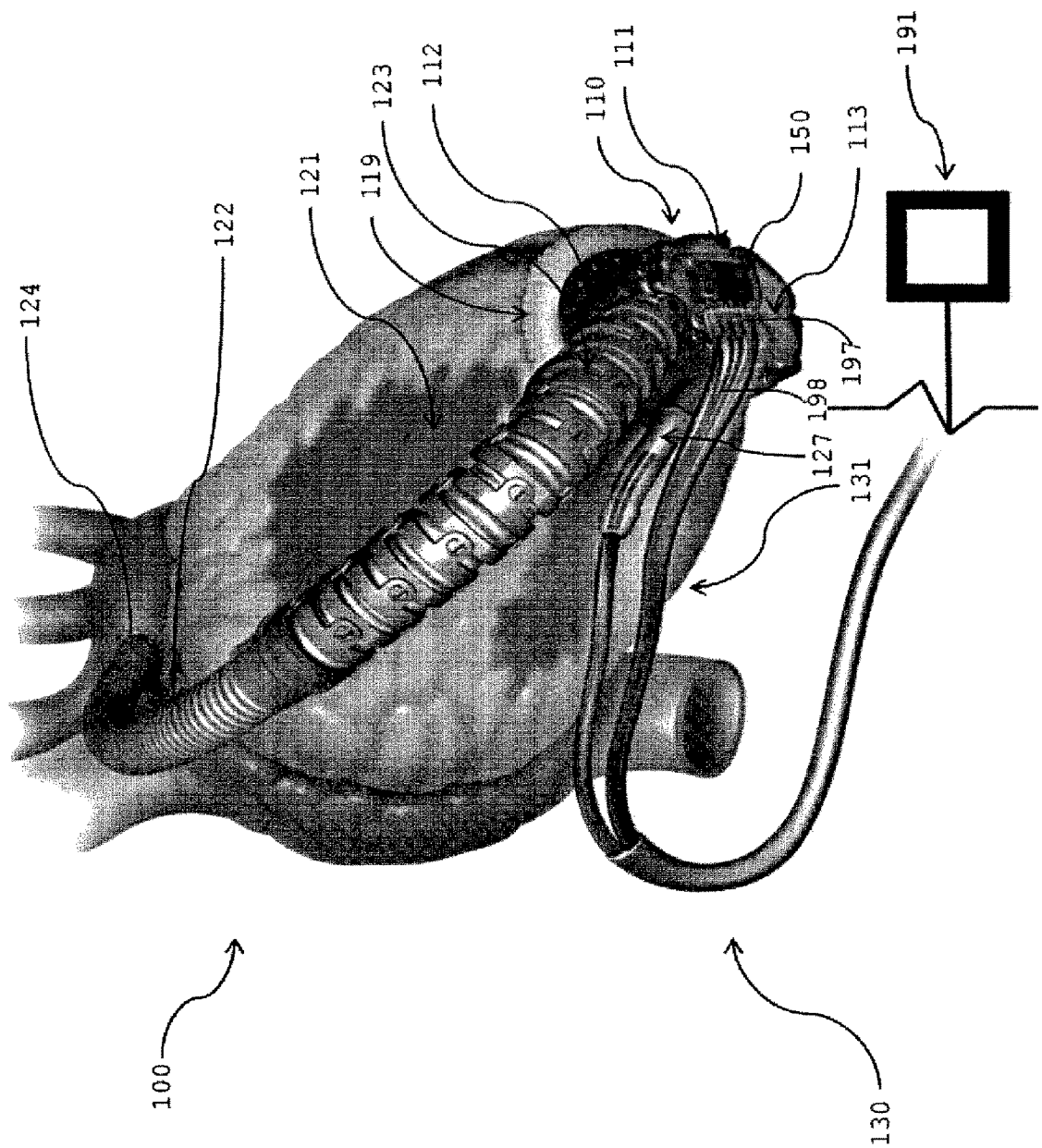
FIG. 1 is a perspective view of a blood pump usable as a ventricular assist device in accordance with one embodiment of the invention, in conjunction with the heart and certain blood vessels of a human patient.

FIG. 1 illustrates an implantable blood pump usable as a ventricular assist device ("VAD") 100 in accordance with one embodiment of the invention. In this embodiment, the VAD 100 comprises a pump 110 having an outer housing 111 that includes and a first or lower housing element 113 and a second or upper housing element 112. The housing elements are formed from biocompatible rigid materials such as titanium or a hybrid titanium-ceramic. The upper housing 112 may further comprise an inflow end 114 (FIG. 2) defining an inlet opening 107. In the implanted condition depicted in FIG. 1, the inflow end of the pump is inserted into heart of a mammalian subject such as a human patient, typically into the left ventricle so that the inflow opening is in communication with the interior of the ventricle. The VAD 100 may also include an apical ring 119 for securing the connection between the outer housing 111 of the pump and the heart. The sewing ring typically is sutured in place on the apex of the heart, and may include a clamp to secure the outer housing 111 to the sewing ring and thus secure the pump in place relative to the heart.

The VAD 100 may also include an outflow conduit 121 extending from the outer housing 111. The outflow conduit 121 may comprise a flexible, biocompatible main tubing 122. The main tubing 122 may also be encased along a portion of its length by an anti-kinking conduit 123. The anti-kinking conduit 123 may be made by plastic interlocking links to prevent kinking. The main tubing 122 may further be surgically attached to a desired position 124 of the heart or the surrounding area, such as to the ascending aorta as depicted in FIG. 1.

The VAD 100 may further include a cable 130, also referred to herein as a driveline. Driveline 130 typically includes a plurality of electrical conductors 131. The driveline 130 electrically connects components of the pump 110 within the outer housing 111 to an external control unit 191. Control unit 191 is arranged to supply electrical power to the pump, and to control the operation of the pump. All or part of control unit 191 may be implanted within the body of the subject, or may be external to the subject.

Figure 2:
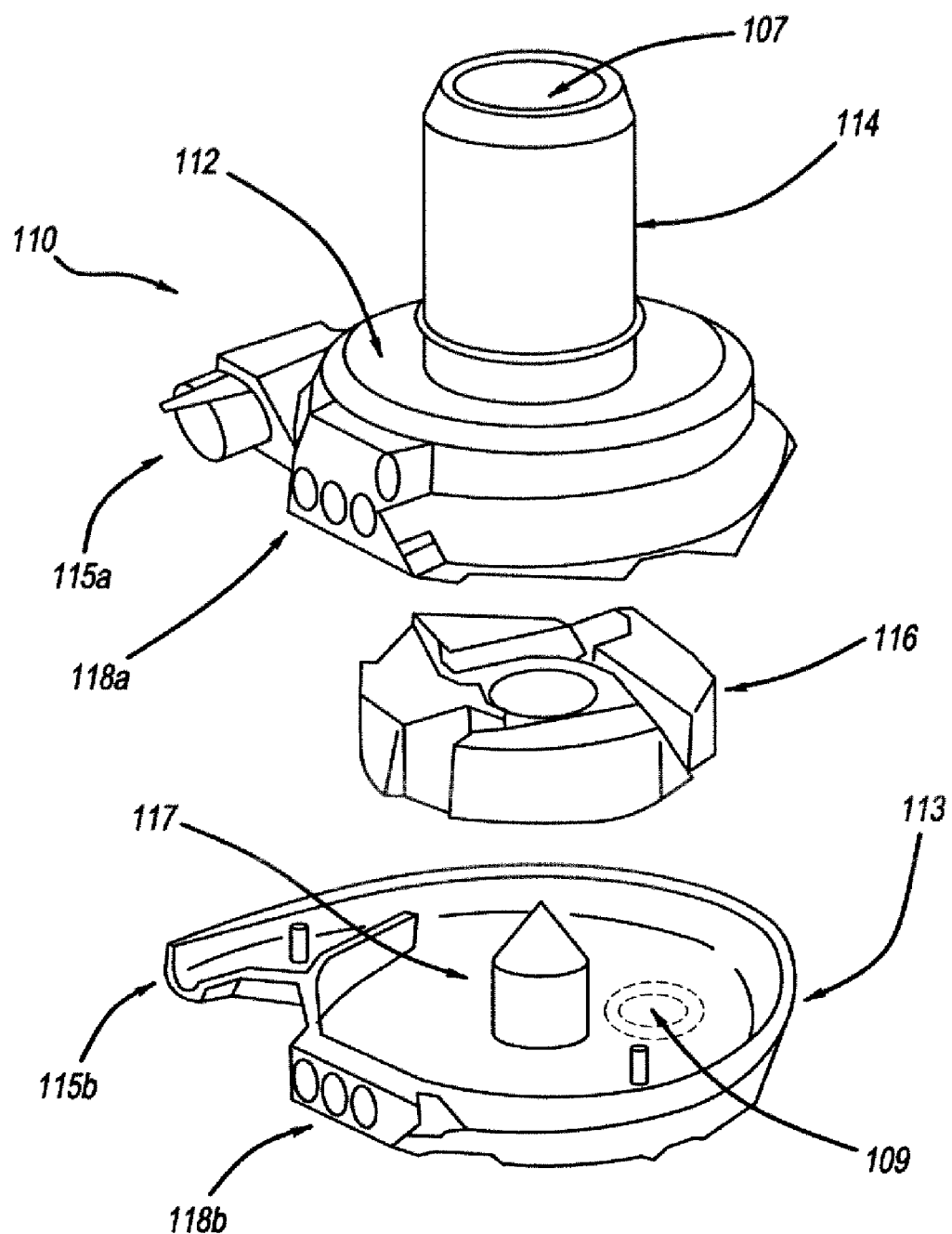
FIG. 2 is an exploded view of pump used in the ventricular assist device of FIG. 1.
Figure 3:
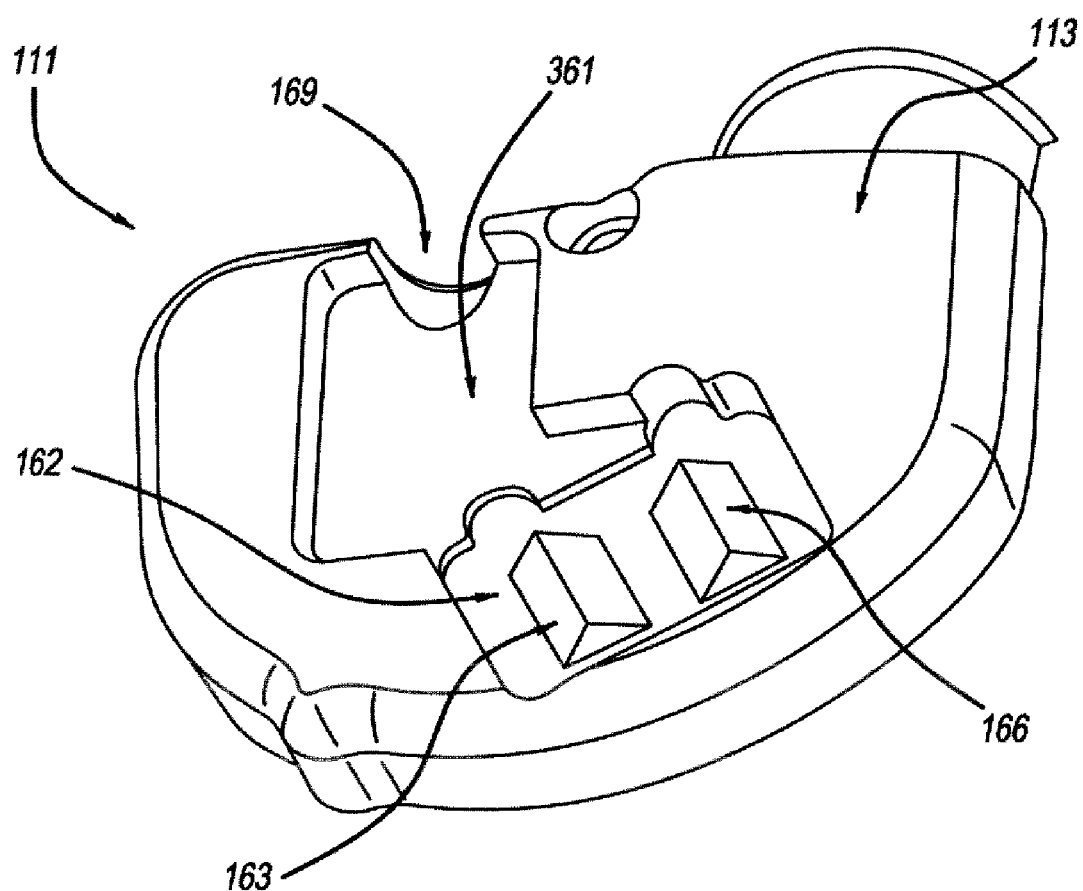
FIG. 3 is a fragmentary perspective view depicting a portion of the ventricular assist device of FIGS. 1 and 2.

As shown in FIG. 2 upper housing element 112 and lower housing element 113 define a flow path therein, which extends from the inlet opening 107 to an outflow end 115a and 115b cooperatively defined by the housing elements 112 and 113. Permanent magnets (not shown) may be provided within one or both of the housing elements 112 and 113, along with a set of electromagnet coils, one of which is schematically represented at 109. In one embodiment, a permanent magnet stack may be contained within a center-post 117 on the lower housing element 113. Pump 110 further includes a movable element 116 for impelling the blood along the flow path. In this embodiment, the movable element 116 is a wide-bladed impeller, which incorporates permanent magnets (not shown). The permanent magnets within impeller 116 cooperate with the permanent magnets in the housing elements to keep impeller 116 suspended and out of contact with the housing elements during operation. When the coil set 109 is energized with alternating current, the magnetic interaction between the coil set and the permanent magnets of the impeller spin the impeller around its axis, so that the impeller will drive blood along the flow path.

The upper 112 and lower 113 housing may further define a driveline interface 118a and 118b for receiving a power connector 127 on the driveline into the pump housing. In one embodiment, the upper housing 112 defines a top portion of the driveline interface 118, and the lower housing 113 defines a bottom portion of the driveline interface 118b. The driveline interface 118 is provided with appropriate terminals (not shown) for making electrical contact with certain conductors of driveline 130 at power connector 127. These terminals are electrically connected to the coil set.

Figure 4:
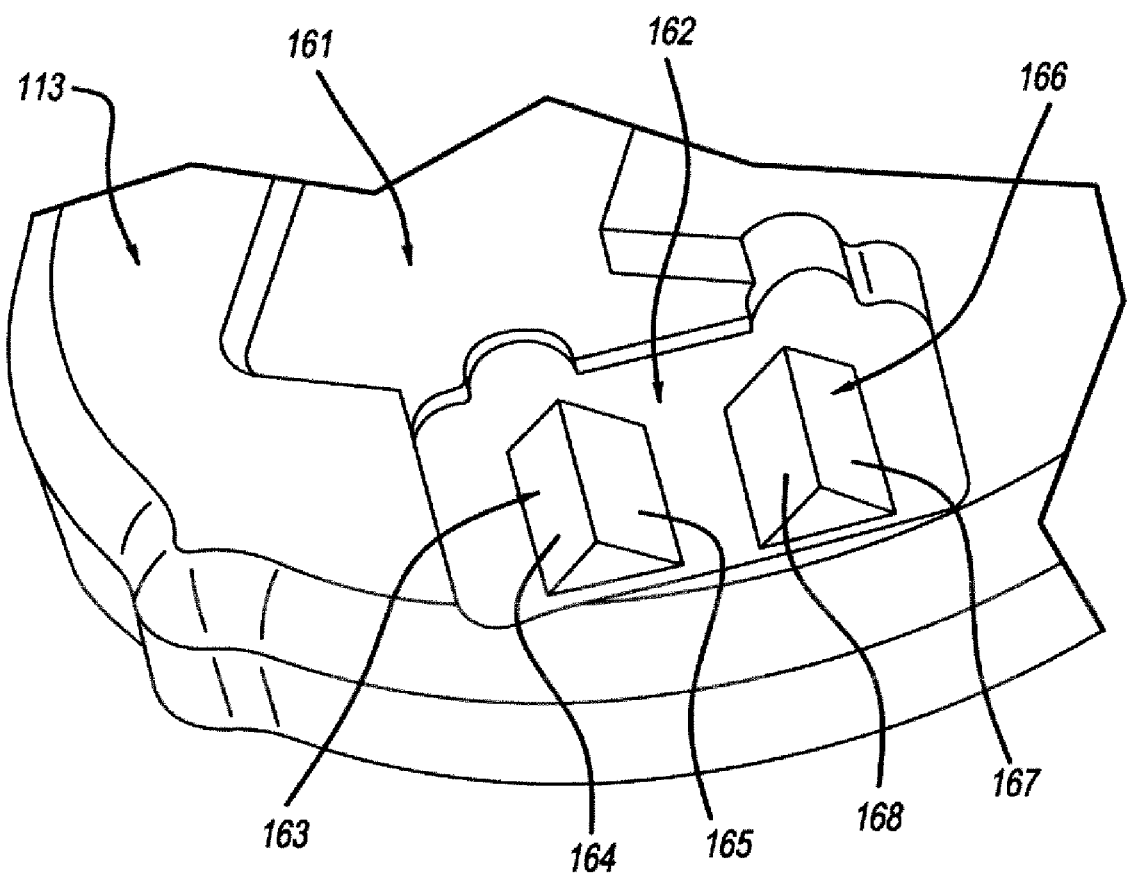
FIG. 4 is a detailed view of the ventricular assist device shown in FIGS. 1-3, on a further enlarged scale.
Figure 5:
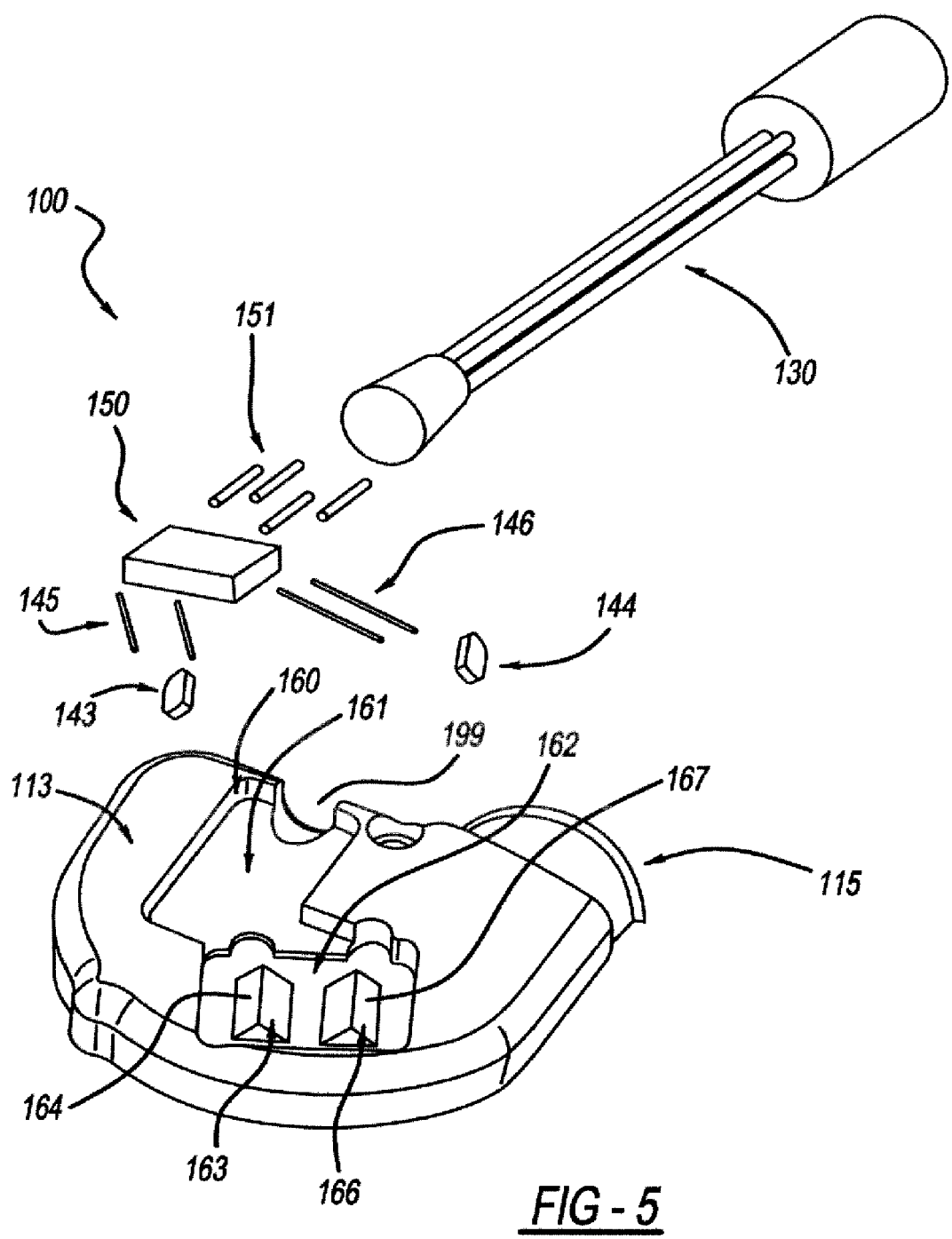
FIG. 5 is a partial exploded view of the ventricular assist device of FIGS. 1-4.
Figure 6:
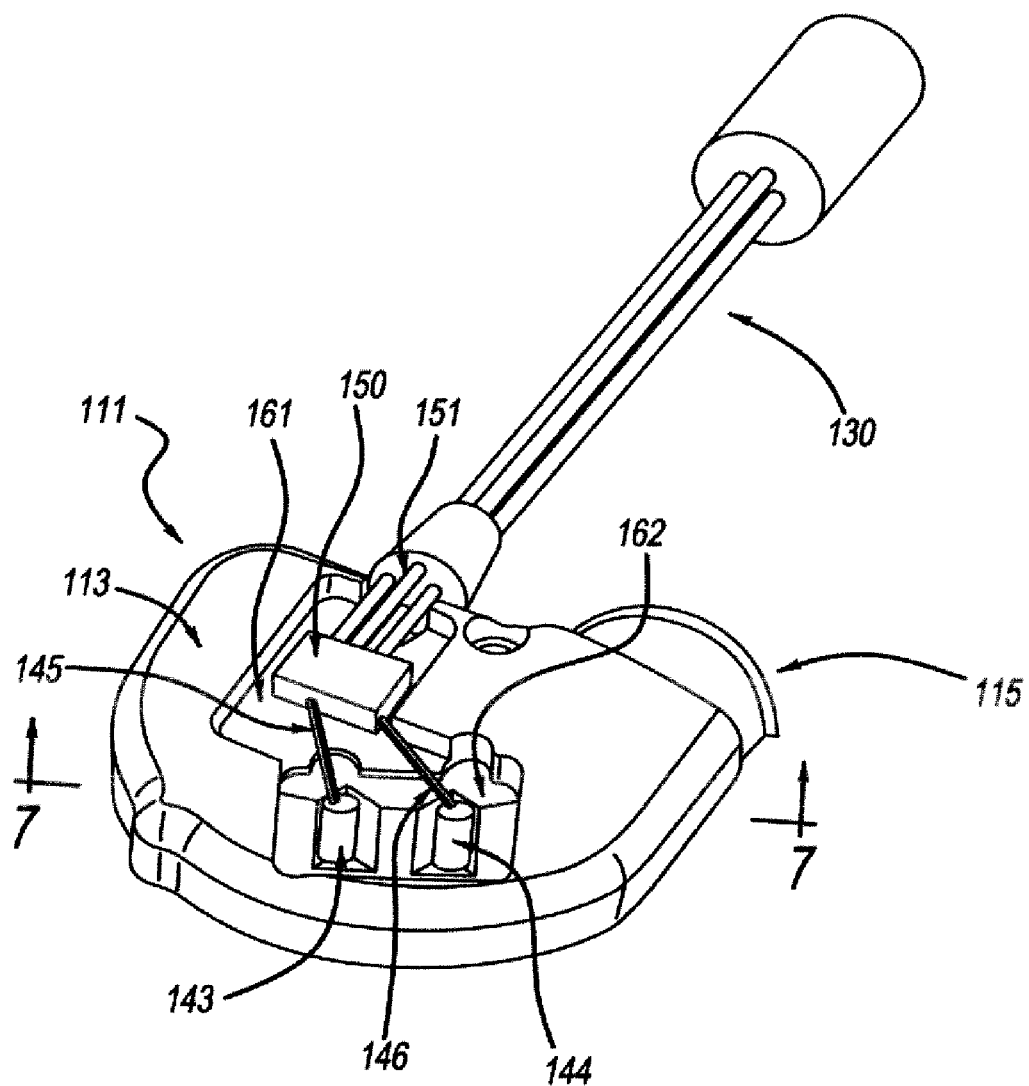
FIG. 6 is a partial assembled view of the ventricular assist device shown in FIGS. 1-5.
Figure 7:
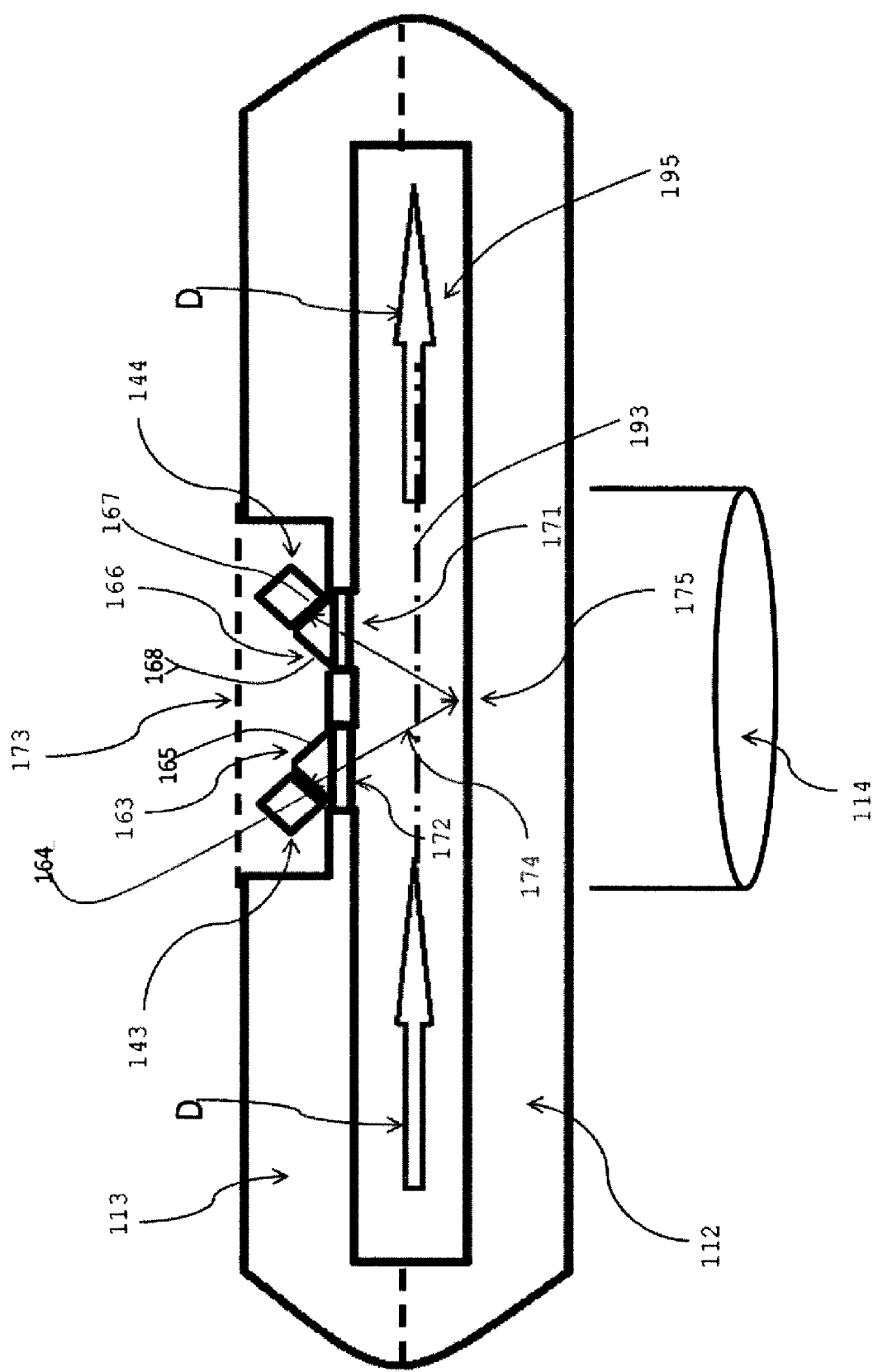
FIG. 7 is a diagrammatic cross-sectional view of the ventricular assist device shown in FIGS. 1-6 accordance with one embodiment of the invention.

As shown in FIGS. 3-8, and as further discussed below, the pump is provided with a flow sensor carried on or within the housing 111. In each of FIGS. 3-6, the first or lower housing element 113 is front facing and visible. In this embodiment, the exterior surface of lower housing element 113 has a PCB cavity 361 and a further cavity 162 which accommodates a first platform 163 and a second platform 166. In one embodiment, cavity 162 is about 0.5 mm in depth. Preferably, the first 163 and second 166 platforms have a height less than or equivalent to the depth of the cavity 166 so that the platforms may be fully accommodated within the cavity 162. As best appreciated with reference to FIG. 7, platforms 163 and 166 overlie a portion 195 of the flow path cooperatively defined by housing elements 112 and 113. This portion of the flow path is adjacent the outflow end 115a, 115b depicted in FIG. 2. Within this portion 195 of the flow path, the blood flows in a downstream direction indicated by arrows D in FIG. 7, generally along a flow path axis 193. As best seen in FIGS. 4 and 7, the first platform 183 defines a first surface 164 facing away from flow path 195 and facing generally upstream (the direction opposite to arrows D) at an angle oblique to the flow path axis 193, as well as a second surface 165. The second platform 166 is disposed downstream from the first platform. Second platform 166 defines a first surface 167 facing away from the flow path and facing downstream at an angle oblique to the flow path axis 193, and also defines a second surface 168. For example, the first surface of each platform may be disposed at an angle of 45 degrees to the axis of the flow path.

A window 172 (FIG. 7) forms an interface between the first platform 163 and the interior of the flow path, and another window 172 forms an interface between the second platform and the flow path. Although the windows are depicted as separate elements from the platforms for clarity of illustration, the windows may be formed integrally with the platforms. Also, the surfaces of the windows bounding the flow path desirably are flush with the surrounding surfaces of housing element 113.

The windows and platforms may be formed integrally with first housing element 113 or may be fixed directly to this housing element. The materials of the platforms and windows desirably provide a low-impedance path for ultrasound between first surfaces 164 and 187 and the interior of the flow path when the flow path is filled with blood. For example, the materials of the platforms and windows may have acoustic impedance reasonably close to that of blood so as to minimize reflection of ultrasound at the interface with the blood within the flow path. For example, the platforms and windows may be formed by casting a biocompatible polymer.

A first ultrasonic transducer 142 is bonded to the first surface 164 of the first platform 163, whereas a second ultrasonic transducer 144 is bonded to the first surface 167 of the second platform 166. The ultrasonic transducers may be conventional piezoelectric elements. The transducers are electrically connected by conductors 145 and 146 to electronic components on a printed circuit board 150 (FIGS. 5 and 6) which is disposed in cavity 161 of housing element 113. The components on the printed circuit board may include conventional components for driving one of the transducers (referred to herein as the "driven transducer") at an ultrasonic frequency, typically in the megahertz range with an electrical signal, and for amplifying electrical signals from the other one of the transducers (referred to herein as the "receiving transducer"). The electronic components may also include components for comparing the phase of the electrical signals from the receiving transducer with the phase of the signals applied to drive the driven transducer.

Printed circuit board 150 is connected by conductors 151 to conductors 198 of driveline 130 at a connector 197 engaged in an opening 199 (FIG. 5) communicating with cavity 561. In this embodiment, connector 197 is separate from the power connector 127 (FIG. 1) engaged with the driveline interface 118 (FIG. 2). The conductors associated with connectors 197 and 127 extend within the outer sheath of driveline 130 over most of the length of the driveline, and diverge from one another only in the immediate vicinity of the pump. Conductors 198 of the driveline link the components on PCB 150 with an appropriate circuit in the control unit 191 (FIG. 1).

A cover schematically indicated at 173 (FIG. 7) overlies cavities 161 and 162, and thus forms a part of the housing which cooperates with housing element 113 to enclose the platforms, transducers, printed circuit board and associated conductors. Cover 173 may be a biocompatible potting material such as an epoxy, or may be a plate fixed to housing element 113 by appropriate fasteners and sealed by an appropriate gasket to prevent entry of body fluids into the cavities 161 and 162.

In operation, with the pump operating and forcing blood through the flow path, the control unit actuates the components on PCB 550 to drive one of the transducers. For example, the control unit and components on PCB 550 may cause the first or upstream transducer 143 to emit ultrasonic waves. These waves pass along a path 174 at an oblique angle to the direction of the blood flow (the downstream direction) and impinge on the wall of the flow path defined by the second or upper housing element 112 at a point 175. The ultrasonic waves are reflected along a further portion of path 174, also oblique to the downstream direction, back to the receiving transducer, in this case the second or downstream transducer 144. The receiving transducer converts the ultrasonic waves to electrical signal. Because the path from the driven transducer to the receiving transducer has a component parallel to the direction of flow of the blood, the time of flight of the ultrasonic waves is influenced by the velocity of the blood according to the well-known Doppler effect. This causes the phase of the received ultrasonic waves to vary with the blood velocity, and thus with the flow rate. Because the housing elements 112 and 113 are rigid, the geometry of the system is fixed. As used in this disclosure, the term "rigid" should be understood as meaning that the housing elements do not distort in normal operation of the pump to a degree which would appreciably affect the phase difference between the received and emitted ultrasonic waves. The mathematical relationships used to convert phase difference to flow velocity, and to convert flow velocity to flow rate, are well known. The circuits used to measure phase difference are also well known and accordingly are not further described herein.

Because the flow measurement is performed by the ultrasonic sensors mounted in the pump housing, there is no need for a separate flow measurement device mounted along the outflow cannula. Moreover, because the connection between the flow sensor and the control unit is made through conductors of the same driveline used to convey power to the pump, there is no need to implant a separate cable leading to a flow sensor.

In a variant of the embodiment discussed above, the connectors 197 and 127 may be integrated into a single connector, mated to a single driveline interface on the pump housing. In yet another variant, conductors of the driveline which convey power pump coil system may also be used to convey ultrasonic frequency electrical signals to and from the PCB or the transducers in a multiplexing arrangement. In yet another embodiment, the PCB 150 may also be used to convey power to the electrically driven elements of the pump itself, such as the coil set 109 schematically shown in FIG. 2.

Also, although the pump depicted in FIGS. 1-7 is a radial-flow impeller pump, the invention can be applied in other pumps, such as an axial-flow impeller pump as depicted in the aforementioned U.S. Pat. No. 8,419,609, and in conjunction with pumps such as diaphragm pumps and piston pumps. Further, although the invention has been described with reference to an ultrasonic flow sensor having two ultrasonic transducers, other types of flow sensors may be mounted to the pump housing. For example, flow sensors which measure the rate of heat transfer to the flowing blood from a heated element can be employed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A blood pump comprising:
   a housing defining a flow path, the housing including a first housing element joined to a second housing element, and a cavity disposed on an exterior surface of the second housing element, the housing further including a window disposed between the second housing element and the cavity;
   a cover overlying the cavity and engaged to the housing;
   a flow sensor disposed within the cavity and angled toward the flow path;
   a driveline proximate the housing, the driveline being in communication with the flow sensor; and
   a control unit coupled to the driveline.

2. The blood pump of claim 1, further comprising a first platform disposed within the cavity, the first platform having the flow sensor coupled thereto.

3. The blood pump of claim 2, wherein the flow path includes an upstream portion and a downstream portion defining a flow path axis extending therethrough, and the first platform includes a surface facing at an angle oblique to the flow path axis.

4. The blood pump of claim 3, further comprising a second platform disposed within the cavity proximate the first platform, the second platform including a second flow sensor coupled thereto, the second flow sensor in communication with the flow sensor.

5. The blood pump of claim 4, further comprising a second window disposed between the second platform and the flow path.

6. The blood pump of claim 4, wherein the second platform is disposed downstream from the first platform, the second platform including a surface facing downstream at an angle oblique to the flow path axis.

7. The blood pump of claim 1, further comprising a second cavity including a printed circuit board having a plurality of conductors coupled to the flow sensor.

8. The blood pump of claim 1, wherein the cover is made of a biocompatible material.

9. The blood pump of claim 1, wherein the cavity includes a first platform and a second platform disposed therein, the first platform and the second platform each having a height selected from the group consisting of:
   a height less than a measured depth of the cavity; and
   a height equivalent to the measured depth of the cavity.

10. A blood pump comprising:
    a housing defining:
       a flow path therethrough from an upstream direction to a downstream direction;
       a first housing element joined to a second housing element; and
       a cavity disposed on an exterior surface of the second housing element and exterior to the flow path; and
    a cover overlying the cavity and engaged to the housing;
    a first flow sensor disposed within the cavity in communication with the flow path; and
    a second flow sensor disposed within the cavity in communication with the first flow sensor.

11. The blood pump of claim 10, further comprising a window disposed between the first flow sensor and the cavity.

12. The blood pump of claim 10, further comprising a first platform and a second platform proximate the first platform, the first platform having a first surface facing the upstream direction and including the first flow sensor being coupled thereto and the second platform including a first surface facing the downstream direction and including the second flow sensor being coupled thereto.

13. The blood pump of claim 12, wherein the housing defines a flow path axis extending through the flow path from the upstream direction to the downstream direction, and the first surface of the first platform and the first surface of the second platform are disposed at an angle oblique to the flow path axis.

14. The blood pump of claim 10, further comprising a second cavity proximate the cavity, the second cavity including a printed circuit board and a plurality of conductors disposed therein, the plurality of conductors coupling the first flow sensor and the second flow sensor to the printed circuit board.

15. The blood pump of claim 14, further comprising a driveline coupled to the printed circuit board in communication with the first flow sensor and the second flow sensor.

16. The blood pump of claim 15, further comprising a control unit coupled to the driveline.

17. The blood pump of claim 10, wherein the first flow sensor is a driving transducer and the second flow sensor is a receiving transducer.

* * * * *